United States Patent [19]

Ringlien

[11] Patent Number: 5,753,905
[45] Date of Patent: *May 19, 1998

[54] OPTICAL INSPECTION OF CONTAINER FINISH DIMENSIONAL PARAMETERS

[75] Inventor: James A. Ringlien, Maumee, Ohio

[73] Assignee: Owens-Brockway Glass Container Inc., Toledo, Ohio

[*] Notice: The term of this patent shall not extend beyond the expiration date of Pat. No. 5,610,391.

[21] Appl. No.: 814,073

[22] Filed: Mar. 10, 1997

Related U.S. Application Data

[62] Division of Ser. No. 296,297, Aug. 25, 1994, Pat. No. 5,610,391.

[51] Int. Cl.[6] .................................................. G01N 9/04
[52] U.S. Cl. ........................ 250/223 B; 250/208.1; 356/240
[58] Field of Search ..................... 250/208.1, 223 B; 356/239, 240, 384, 385

[56] References Cited

U.S. PATENT DOCUMENTS

| | | |
|---|---|---|
| 4,064,534 | 12/1977 | Chen et al. . |
| 4,230,219 | 10/1980 | Pezzin et al. . |
| 4,376,951 | 3/1983 | Miyazawa . |
| 4,378,493 | 3/1983 | Dorf et al. . |
| 4,386,828 | 6/1983 | Hirose . |
| 4,492,476 | 1/1985 | Miyazawa . |
| 4,526,443 | 7/1985 | Hirose . |
| 4,608,709 | 8/1986 | Hedler et al. ............. 250/223 B |
| 4,701,612 | 10/1987 | Sturgill . |
| 4,725,856 | 2/1988 | Fujikura . |
| 4,792,695 | 12/1988 | Blandford . |
| 4,906,098 | 3/1990 | Thomas et al. . |
| 4,958,223 | 9/1990 | Juvinall et al. . |
| 5,008,743 | 4/1991 | Katzir et al. . |
| 5,610,391 | 3/1997 | Ringlien ...................... 250/223 B |

FOREIGN PATENT DOCUMENTS

| | | |
|---|---|---|
| 0456910A1 | 11/1991 | European Pat. Off. . |
| 1-31040 | 2/1989 | Japan . |
| 2065299 | 12/1979 | United Kingdom . |
| 2157824 | 10/1985 | United Kingdom . |

OTHER PUBLICATIONS

European Search Report dated Mar. 27, 1997.

*Primary Examiner*—Stephone B. Allen

[57] ABSTRACT

Apparatus for inspecting external dimensional parameters of a container finish that includes a light source for directing light energy onto the finish of the container and a matrix array sensor disposed to receive an image of the container finish illuminated by the light source. A telecentric lens is positioned to focus onto the matrix array sensor an image of the container finish profile formed by light energy traveling parallel to the telecentric lens axis, such that the finish profile appears as a dark image against a light background at the sensor. The matrix array sensor is scanned at increments of container rotation to determine one or more dimensional parameters of the container finish.

2 Claims, 1 Drawing Sheet

OPTICAL INSPECTION OF CONTAINER FINISH DIMENSIONAL PARAMETERS

This is a division of application Ser. No. 08/296,297 filed Aug. 25, 1994,now U.S. Pat. No. 5,610,391.

The present invention is directed to non-contact measurement of container dimensional parameters, and more particularly to an apparatus and method for optical measurement of external dimensions of a container finish profile.

BACKGROUND AND SUMMARY INVENTION

In the art of container manufacture, the term "container finish" generally refers to that portion of the container that defines the container mouth. In a bottle, for example, the finish includes that portion of the container neck having threads and/or shoulders for receiving the container cap, as well as the upper surface of the neck surrounding the container mouth against which the cap seats. It is important that the container finish be properly manufactured and possess desired external geometric characteristics so that a cap may be affixed thereto to seal the container against leakage and escape of carbonation during handling and storage.

U.S. Pat. No. 4,701,602, assigned to the assignee hereof, discloses a method and apparatus for inspecting the finish of transparent containers, particularly glass containers, which include facility for directing diffused light energy laterally through the container finish as the container is rotated about its central axis. A camera includes a plurality of light sensitive elements or pixels disposed in a linear array angulated with respect to the container axis and coplanar therewith to view the external and internal wall surfaces, the latter through the open container mouth. Individual elements of the camera linear array are sampled by an information processor at increments of container rotation, and corresponding data indicative of light intensity at each element is stored in an array memory as a combined function of element number and scan increment. Such data is compared following completion of container rotation to standard data indicative of an acceptable container finish, and a reject signal is generated if such comparison exceeds an operator-adjustable threshold.

U.S. Pat. No. 4,958,223, also assigned to the assignee hereof, discloses a method and apparatus for inspecting the finish of a container as the container is held and rotated about its central axis. A light source is positioned to direct diffused light energy onto the container finish, and a camera is positioned across the axis of the container from the light source. The camera comprises a matrix array sensor positioned with respect to the camera focusing elements to receive an image of the container finish as illuminated by the light source. Information processing electronics are coupled to the camera array for indicating optical characteristics of the container finish as differing functions of light intensity incident on the matrix elements for detecting structural commercial variations or geometric parameters of the container finish.

Although the systems so disclosed in the noted patents represent significant advances as compared with previous finish inspection techniques, further improvements remain desirable. For example, in applications in which it is specifically desired to measure external dimensional parameters of the container finish, as opposed for example to internal structural variations in the container finish area, it is highly desirable to develop a sharp image of the container profile—i.e., an image in which transition at the profile edges is characterized by high contrast and sharp transition between light and dark. A general object of the present invention is to provide a system and method that is characterized by such a sharp transition at the profile image edges, and thus are adapted for obtaining improved and enhanced measurement accuracy of finish profile dimensional parameter measurements.

Apparatus for inspecting external dimensional parameters of a container finish in accordance with the present invention includes a light source for directing light energy onto the finish of the container and a matrix array sensor disposed to receive an image of the container finish illuminated by the light source. A telecentric lens and camera lens combination is positioned to focus onto the matrix array sensor an image of the container finish profile formed by light energy traveling parallel to the telecentric lens axis, such that the finish profile appears as a dark image against a light background at the sensor. The matrix array sensor is scanned, preferably at increments of container rotation, to develop multiple electronic two-dimensional images of the finish profile, each from a different azimuthal position with respect to the finish, from which one or more dimensional parameters are determined. Use of the telecentric lens arrangement effectively to reject light rays that are non-parallel to the optical axis of the lens and camera provides an image of the container finish that is characterized by high contrast between the dark image and the light background, and a sharp non-ambiguous transition at the profile edges.

BRIEF DESCRIPTION OF THE DRAWING

The invention, together with additional objects, features and advantages thereof, will be best understood from the following description, the appended claims and the accompanying drawing in which:

DETAILED DESCRIPTION OF PREFERRED EMBODIMENTS

Figure 1:
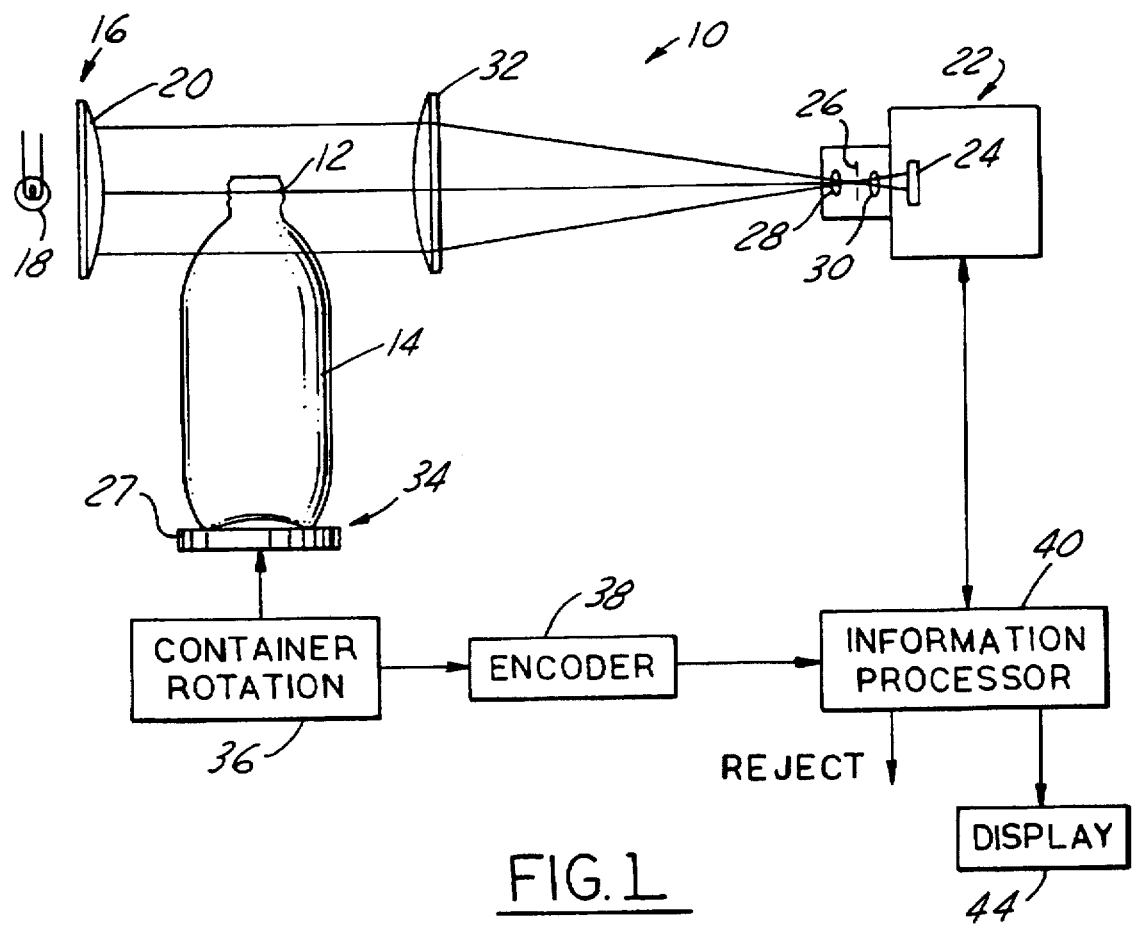
FIG. 1 is a schematic diagram of an electro-optical non-contact system for measuring external dimensional parameters of a container finish in accordance with a presently preferred embodiment of the invention.

FIG. 1 illustrates an apparatus 10 for measuring dimensional parameters of the finish 12 of a container 14 in accordance with a presently preferred embodiment of the invention. A light source 16 is disposed to direct light energy onto the container finish from a direction generally orthogonal to the container axis. Light source 16 may comprise one or more lamps and a diffuser of limited width, or more preferably may comprise a single lamp 18 disposed at the focus of a lens 20 for transmitting substantially parallel light rays onto container finish 12. Light source 16 may be of constant illumination or strobed. A camera 22 is positioned across container 14 from light source 16. Camera 22 includes a matrix array CCD sensor 24, an entrance pupil 26 and lenses 28,30 associated with entrance pupil 26.

A telecentric lens 32 is positioned between camera 22 and container finish 12. Telecentric lens 32 has a first focus in the direction of container 14 at infinity, and a second focus at entrance pupil 26. That is, camera 22 is positioned with respect to lens 32 so that entrance pupil 26 is spaced from lens 32 by the focal distance of the lens. Thus, pupil 26 with lenses 28,30 functions as an iris in combination with lens 32 for focusing onto sensor 24 essentially only light rays from light source 16 that travel past finish 12 parallel to the optical axis of lens 32 and camera 22. That is, light rays that impinge upon container 14 are reflected, absorbed and/or refracted, so that the light rays do not emerge from the container in a direction parallel to the lens/camera axis. Camera 22 is positioned such that sensor 24 is at the image of the container finish as seen through telecentric lens 32. Thus, sensor 24 receives a sharp image of the container finish profile formed as a dark image against a light background.

A conveyor 34, typically including a starwheel (not shown) and a slide plate 27, is so disposed and connected to a source of molded containers as to bring successive containers 14 into position at apparatus 10. Conveyor 34 may be of any suitable type, such as those shown in U.S. Pat. Nos. 4,230,219 and 4,378,493. Successive containers are held in fixed position and rotated by a device 36, such as a drive roller, about the central axis of the container. An encoder 38 is coupled to the container rotation mechanism to provide signals indicative of increments of container rotation. An information processor 40 is coupled to encoder 38 and to matrix array sensor 24 for scanning the sensor at increments of container rotation and developing multiple two-dimensional electronic images of the container finish from different azimuthal positions with respect to the finish. As an alternative to use of encoder 38, information processor 40 may be controlled to scan sensor 24 at substantially equal increments of time while container 14 is rotated at substantially constant velocity.

Figure 2:
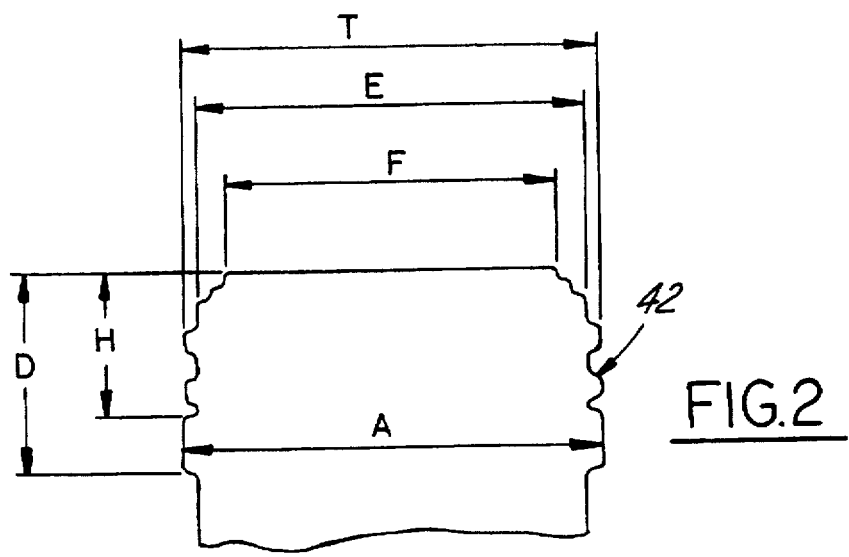
FIG. 2 is a schematic diagram of the container finish profile illustrating exemplary dimensional parameters that can be measured in accordance with the present invention.

There are thus developed at information processor 40 multiple two-dimensional electronic images of the container finish, as illustrated schematically at 42 in FIG. 2. Such images may be displayed at 44 (FIG. 1) and/or analyzed using suitable techniques to generate a container reject signal in the event that one or more container finish dimensional parameters are unsatisfactory. Exemplary techniques for scanning matrix array sensor 24 and developing two-dimensional electronic images 42 of the container finish profile are disclosed in above-noted U.S. Pat. No. 4,958,223.

FIG. 2 illustrates exemplary dimensional parameters of the container finish image 42 that may be measured and analyzed in accordance with the present invention. The dimensional parameters are designated by the Glass Packaging Institute Standard Code Letters A (bead diameter), D (crimping ledge height), E (thread base wall diameter), F (top and side seal diameter), H (top to bead closure clearance) and T (thread diameter). Other standard or non-standard parameters may also be measured. Since the container finish refracts, reflects and/or absorbs light from source 16 that impinges on the container, so that any light rays that emerge from the container will not be parallel to the optical axis of lens 32 and camera 22, and thus not directed onto sensor 24, the edge contrast at image 42 between the dark profile of the container finish and the light background is very distinct and sharp. Thus, container finish dimensional parameters are measurable with significantly increased accuracy and precision as compared with prior art technique heretofore proposed.

I claim:

1. Apparatus for inspecting external finish dimensional parameters of hollow glass containers that comprises:

means for presenting containers in sequence at an inspection station, means for directing collimated light energy onto the exterior of the finish of a container at said station such that a first portion of such light energy travels past the finish exterior while a second portion is incident on the finish exterior and reflected or refracted by the container finish such that light rays in said second portion are no longer parallel to collimated light rays in said first portion, means for focusing through an iris onto a matrix array sensor said first portion of said collimated light energy that travels past the container finish exterior at said station in a direction parallel to an optical axis of said sensor, and thereby excluding from light energy focused onto said sensor said second portion of said collimated light energy that is reflected or refracted by the container finish, such that the exterior profile of the container finish appears at said sensor as a dark image against a light background.

means for scanning said matrix array sensor to obtain a two-dimensional image of the exterior profile of the container finish, and means for determining at least one exterior dimensional parameter of the container finish from said two-dimensional image.

2. The apparatus set forth in claim 1 further comprising means for rotating the container at said station about the axis of the container, and wherein said scanning means comprises means for scanning said matrix array sensor at increments of container rotation so as to develop multiple two-dimensional images of the container finish exterior profile at increments of container rotation from different azimuthal positions with respect to the finish.

* * * * *